United States Patent [19]
Arnaout et al.

[11] Patent Number: 5,091,303
[45] Date of Patent: Feb. 25, 1992

[54] DIAGNOSIS OF WEGENER'S GRANULOMATOSIS

[75] Inventors: M. Amin Arnaout, Chestnut Hill; Robert T. McCluskey, Brookline; John L. Niles, Cambridge, all of Mass.

[73] Assignee: The General Hospital Corporation, Boston, Mass.

[21] Appl. No.: 428,286

[22] Filed: Oct. 27, 1989

[51] Int. Cl.$^5$ .................. C07K 15/06; C12N 9/64; G01N 33/564; G01N 33/577

[52] U.S. Cl. .................. 435/7.24; 435/7.4; 435/23; 435/226; 435/975; 436/506; 436/518; 436/536; 436/548; 530/350; 530/387; 530/806; 935/110

[58] Field of Search .................. 435/7.4, 23, 226, 975; 436/506, 518, 548, 536; 530/350, 387, 403, 806, 809; 935/110

[56] References Cited

U.S. PATENT DOCUMENTS 4,452,901  6/1984  Gordon et al. .................. 436/506
4,784,942  11/1988  Harley .................. 436/506

OTHER PUBLICATIONS

Gans et al, *The Lancet*, vol. I, 269-270, 3-1989.
Goldschmeding et al, *Kidney Int.*, 34, 558, 1988.
van der Woude et al. (1-1988) Lancet I:425-429.
Andrassy et al. (11-1988) Nephron 49:257-258.
Falk et al. (12-1988) New Engl. J. Med. 318:1651-1657.
Gross et al. (3-1987) Lancet I:1488-1489.
Goldschmeding et al. (2-1987) Kindey Int 32:779 (abstract).
Ludemann et al. (6-1988) J. Immuno. Methods 114:167-174.
Nolle et al. (4-1989) Annals of Internal Medicine 111:28-39.
Davies et al. (3-1982) British Medical Journal 285:606.
Ludemann et al. (2-1987) Clin. Exp. Immunol. 69:350-357.
Parlevliet et al. (2-1988) Quarterly J. of Medicine 66:55-63.
Hall et al. (1-1984) Aust. NZ J. Med. 14:277-278.
Lockwood et al. (11-1987) Lancet I:716-719.

*Primary Examiner*—David Saunders
*Attorney, Agent, or Firm*—Fish & Richardson

[57] ABSTRACT

A purified protein (p29) capable of binding autoantibodies present in the sera of individuals suffering from Wegener's granulomatosis. The invention also features a monoclonal antibody against the p29 protein and methods of diagnosing Wegener's granulomatosis.

4 Claims, 1 Drawing Sheet

FIG. I

| P29 | I V G G H E A Q P H S X P Y M A S L Q M |
|---|---|
| LEUKOCYTE ELASTASE | I V G G R R A R P H A W P F M V S L Q L |
| Cathepsin G | I I G G R E S R P H S R P Y M A Y L Q I |
| COMPLEMENT FACTOR D | I L G G R E A E A H A R P Y M A S V Q L |
| TRYPSIN | I V G G Y T C G A N T V P Y Q V S L N S |
| CHYMOTRYPSIN | I V N G E E A V P G S W P W Q V S L Q D |
| PLASMIN | V V V G G C V A H P H S W P W Q V S L R T |
| COAGULATION FACTOR Xa | I V G G R D C A E G E C P W Q A L L V N |
| THROMBIN | I V E G S N A E I G M S P W Q V M L F R |

I=Ile; V=Val; G=Gly; H=His; E=Glu; A=Ala; Q=Gln; P=Pro; S=Ser; X=unknown;

Y=Tyr; M=Met; L=Leu.

DIAGNOSIS OF WEGENER'S GRANULOMATOSIS

This invention was made with Government support under AI 21963, DK 18729 and DK 38452 awarded by NIH. The Government has certain rights in the invention.

BACKGROUND OF THE INVENTION

This invention relates to the diagnosis of Wegener's granulomatosis.

Wegener's granulomatosis is a disease of unknown cause and pathogenesis. Its major pathologic features are necrotizing granulomatous lesions, which most often affect the upper and lower airways, vasculitis, necrotizing glomerulonephritis and pulmonary capillaritis. Wegener's granulomatosis is a devastating illness, which without the early institution of immunosuppressive therapy can lead to rapid loss of renal function or massive pulmonary hemorrhage. Death occurs in over 80% of untreated patients within one year.

Patients with Wegener's granulomatosis have circulating autoantibodies directed against neutrophils and monocytes. The presence of these autoantibodies are useful in diagnosing the disease. The autoantibodies have usually been detected by indirect immunofluorescence assay, employing ethanol-fixed normal neutrophils as substrates. van der Woude et al. (1985) Lancet 1:425-429. Two staining patterns have been described: (1) cytoplasmic, and (2) nuclear or perinuclear. Andrassy et al. (1988) Nephron 49:257-258. The cytoplasmic pattern is detected in the majority of patients with active Wegener's granulomatosis, and is rarely found in other diseases. In contrast, the nuclear or perinuclear staining pattern is seen in only a very small percentage of patients diagnosed as having Wegener's granulomatosis, and is also observed in some patients with idiopathic necrotizing and crescentic glomerulonephritis, and in periarteritis with glomerulonephritis—so called microscopic polyarteritis. The antigen associated with the nuclear staining pattern has been shown to be myeloperoxidase (MPO), a primary granule component. The nuclear staining pattern results from artifactual redistribution due to ethanol fixation. Falk et al (1988) N. Engl. J. Med 318:1651-1657. The autoantigen associated with the cytoplasmic staining pattern is a soluble protein of 27-29 kilodalton (kD) localized to the primary or secondary granule fractions Gross et al. (1987) Lancet 1:1488-1489; Goldschmeding (1987) Kidney Int. 32:779.

The list of differential diagnosis in Wegener's granulomatosis is extensive and the early presentation can vary from a mild cough to renal failure. Without early treatment the disease is fatal in the vast majority of patients. Treatment, however, involves potentially toxic drugs, and clinicians may be reluctant to proceed without a definitive diagnosis. Accurate diagnosis of the disease is thus vital.

SUMMARY OF THE INVENTION

In general the invention features a substantially pure protein (p29) found in human neutrophils. The protein has a mass of approximately 29 kD as determined by SDS-PAGE, is capable of binding diisopropylfluorophosphate, possesses a pI of approximately 9.2-9.4, is capable of binding to autoantibodies present in the sera of individuals afflicted with Wegener's granulomatosis, and has the N-terminal sequence Ile Val-Gly-Gly-His-Glu-Ala-Gln-Pro-His Ser-X-Pro-Tyr-Met-Ala-Ser-Leu-Gln-Met, where X is unknown. Substantially pure means a preparation with a purity of 95% or greater by weight, substantially free of the proteins, lipids, and carbohydrates with which the protein is naturally associated.

In another aspect the invention features a monoclonal antibody with a binding specificity for p29. Binding specificity for p29 means the monoclonal antibody binds strongly to that protein and is substantially unreactive with other proteins.

In another aspect the invention features a method of detecting autoantibodies diagnostic of Wegener's granulomatosis. The method consists of contacting a biological fluid to be tested to the substantially purified protein of the invention. Any immune complexes formed are detected and used as a measure of the presence of autoantibodies diagnostic of Wegener's granulomatosis in the biological fluid.

In another aspect the invention features a method of detecting autoantibodies diagnostic of the presence of Wegener's granulomatosis. The method consists of: (a) contacting the monoclonal antibody of the invention with its antigen, (b) contacting any immune complexes formed in step (a) with a biological fluid to be tested, and (c) detecting the binding of autoantibodies to the immune complexes formed in (a) as a measure of the presence of autoantbodies diagnostic of Wegener's granulomatosis in the biological fluid.

In another aspect the invention features a vector containing a DNA sequence encoding the p29 protein.

The compounds and methods of the invention provide means of detecting the characteristic autoantibodies of Wegener's granulomatosis that are specific, easily interpreted and quantitative. The usual method of detection of anti-neutrophil cytoplasmic antibodies employs autoantibody staining and indirect immunofluorescence. Interpretation of immunofluorescence findings requires considerable experience and results may vary from one laboratory to another. The interpretation of results in the assays of the invention depend on methods such as conventional solid or liquid phase immunoassay. The results from these techniques are far simpler to interpret than those obtained in indirect immunoflourescence assays of the prior art, where very subtle differences in the pattern of the antibody binding to fixed cellular structures must be identified and distinguished. Furthermore unlike indirect immunofluorescence based methods the assays of the invention are guantitative.

Detection of the disease uses either an affinity purified antigen that binds to the characteristic autoantibodies of the disease or a monoclonal antibody to that antigen. In methods where detection is based on the use of p29 (a single, precisely defined, highly purified antigen) there is no danger that different batches of autoantigen will provide different targets for autoantibody binding, as would be seen with assays using a preparation of antigen that is less pure. In methods that use a monclonal antibody to p29 the results are similarly specific.

Other features and advantages of the invention will be apparent from the following description of the preferred embodiments, and from the claims.

DESCRIPTION OF THE PREFERRED EMBODIMENTS

We turn now to a description of preferred embodiments of the invention, after first briefly describing the drawing.

DRAWING

FIG. 1 is the N terminal sequences of p29 and other serine proteases.

PREPARATION OF A MONOCLONAL ANTIBODY AGAINST THE 29KD PROTEIN

To generate monoclonal antibodies 6 week old female Balb/c mice were immunized each with 10 μg of neutrophil-acid extract (prepared as described below) in complete Freund's adjuvant intradermally in the lower leg. After three boosts over a two-week period, popliteal lymph nodes were isolated, and lymphocytes fused with the NSI mouse plasma cell line (American Type Culture Collection) as described in Kohler et al. (1975) Nature, 256:495–497. After 10–14 days of growth in HAT selective culture medium culture supernatants from hyribdomas were evaluated for antineutrophil activity by Western blot analysis, as described below. Monoclonal antibodies that stained a 29 kD band (p29) which comigrated with the band identified by Wegener's granulomatosis antoantibodies (from sera) were selected Hybridomas with the desired activity were subcloned twice and one monoclonal antibody (mAb), 1IE8, was successfully isolated.

Neutrophil-acid extracts were prepared according to Lockwood et al. (1987) Lancet 1:716–719, and as follows. Briefly $1 \times 10^9$ cells were washed and then sonicated for 5 min. in 0.2M sodium acetate buffer, pH 4.2 at 0° C. (If cells are to be labeled with diisopropylfluorophosphate (DPF) it is added at 5 mM and the cells are held on ice for 10 minutes prior to washing). After centrifugation at 20,000 g for 20 minutes at 4° C., the supernatant was adjusted to pH 7.4, or dialysed against phosphate buffered saline, pH 7.4 (PBS). The concentration of protein in the sample was determined by the method of Lowry.

Western blot analysis of Wegener's granulomatosis autoantibodies was performed as follows. The acid extract, prepared as described above (25 μg/lane), was separated by electrophoresis on sodium dodecyl sulfate polyacrylamide gels (SDS-PAGE) as described in Laemmli (1970) Nature 227:680. Proteins from unstained gels were transferred electrophoretically onto nitrocellulose membranes by the method of Towbin et al. (1979) Proc. Natl. Acad. Sci. U.S.A. 76:4350–4354. The membranes were cut into strips and stained with patients' sera (1:10 dilution) followed by biotinylated secondary antibody and formation of an avidin-biotin-peroxidase complex. The bound antibodies were detected by the chromagen 3 amino 9 ethylcarbazole as a substrate for peroxidase.

Characterization of 1E8, a Monoclonal Anti p29 Antibody

The mAb, 1E8, reacted with a neutrophil-derived 29 kD band on Western blots and produced an immunofluorescent-staining pattern identical to that of autoantibodies from patients' sera. Western blot analysis was performed as described above.

Indirect immunofluorescence analysis was performed as follows. Anti-neutrophil cytoplasmic antibodies were detected by indirect immunofluorescence using cytocentrifuged and ethanol-fixed neutrophils from normal individuals. Neutrophils were isolated by centrifugation on Ficol-Hypague gradients (Pharmacia, Piscataway, N.J.), followed by hypotonic lysis as described in Boyum (1968) Scand. J. Clin. Lab. Invest. 97:77–89. Cytocentrifuge preparations were made using a Shandon Southern cytocentrifuge (Cheshire, England). Each preparation was fixed for five minutes in 100% ethanol, dried, then incubated for one hour at room temperature (RT) with serum (1:16 dilution). After two washes, the cells were stained with fluoresceinated goat anti-human Ig (Meloy, Springfield, Va.) for 60 minutes at RT, washed, and then examined using a fluorescence microscope.

Sera were obtained from ten patients diagnosed as having Wegener's granulomatosis. Clinically, all patients had upper or lower airway disease (nasal erosion, sinisitis, hemoptysis) with or without rapidly progressive renal failure. Pathologically, three patients had characteristic necrotizing granulomatous lesions in nasal biopsies. The remaining seven patients had pathologic evidence of nasal vasculitis or pulmonary capillaritis with or without necrotizing and crescentic glomerulonephritis with scanty or absent immunoglobulin deposits. Sera were also obtained from normal volunteers. All sera were frozen at −20° C. until used.

Sera from ten patients with Wegener's granulomatosis were screened for the presence of autoantibodies reactive with normal neutrophil lysates by Western blots, as described above. All patient's sera were obtained within one month of tissue biopsy. Sera from all ten patients contained autoantibodies against a 29 kD antigen (p29) and produced a cytoplasmic staining pattern in ethanol-fixed neutrohils. No serum from any of 200 normal individuals had anti-p29 antibodies.

Purification of p29, the 29 kD Antigen

The mAb 1E8 was utilized to affinity purify p29 using the method of Schneider et al. (1982) J. Biol. Chem. 257:10766–10769. 1E8 (of the IgG1 subclass) was bound to Sepharose-protein A beads by coupling with dimethylpimmelimidate. A 10 ml column of settled monoclonal antibody-derivatized Sepharose beads was extensively washed, then incubated with 30 mg of neutrophil-acid extract (prepared as detailed above) for three hours at RT. The column was washed with five bed volumes of PBS followed by five-bed-volumes of PBS containing 500 mM NaCl. After re-equalization in PBS, the column was eluted with 0.2M citric acid, pH 2.75, in 1 ml fractions and neutrality was immediately established using Tris base. Eluted protein was detected spectrophotometrically at $OD_{280}$. The desired fractions were pooled and incubated with protein A-Sepharose (to remove trace amounts of contaminating mAb). Pooled fractions were concentrated and dialysed against distilled water using collodion bags. Seven hundred μg of protein were recovered in the eluate.

Characterization of the 29 kD Antigen

The affinity purified antigen recognized by 1E8 migrated on SDS-PAGE as three close bands, with the major component at 29 kD under non reducing conditions. The purified antigen reacted with autoantibodies from patients' sera on Western blots indicating identity between Wegener's granulomatosis autoantigen and the one recognized by 1E8. On isofocusing gels, p29 had a pI of 9.2–9.4.

p29 was shown to be a novel serine proteinase as follows. Ten ug of purified p29 were subjected to 20 cycles of Edman degradation using the Applied Biosystems Model 470 A sequenator. A single N-terminal sequence was obtained (FIG. 1) suggesting that the molecular heterogeneity of the purified protein on SDS-PAGE may reflect isoforms of one protein. Search for homologies using National Biomedical Research Foundation and Swiss protein data banks revealed that the derived sequence represents a novel protein with significant homology to the serine proteinase family. In particular, two hydrophobic residues (isoleucine and valine) are present at the N-terminus, as found at the N-termini of the catalytic chain of all serine proteinases. In addition the invariable residues glycine (at position 4) and; proline (at position 13) are present in p29 (FIG. 1). p29 was clearly distinct from leukocyte elastase and cathepsin G, two neutrophil serine proteinases that are located in primary granules. p29, like leukocyte elastase and cathepsin G, also bound to radiolabelled DFP, as described below.

N terminal sequence determination was performed as follows. One hundred μg of purified p29 were exhaustively dialysed against distilled water, concentrated to 200 μl and 20 μl subjected to SDS-PAGE, dry blotted onto Immobilon-P (Millipore) and stained with India ink. The major p29 band was excised with a razor blade and subjected to 20 cycles of Edman degradation using the Applied Biosystems Model 470 A sequenator. PTH derivatives were resolved by HPLC using a Cyno column (IBM) and Permaphase ETH precolumn (Applied Biosystems, California), with gradient elution (solvent A:70 mM sodium acetate, pH 5.5, 5% v/v tetrahydrofuran; solvent B: acetonitrile; gradient 11-48% over 20 minutes, at a flow rate of 1 ml/minute). The N-terminal sequence obtained from the excised band was identical to that obtained from direct sequencing of the affinity purified protein.

The $^3$H-DFP binding assay was performed as follows. Monoclonal antibody 1E8 was used in a sandwich radioimmunoassay to detect binding of $^3$H-DFP to p29. A sodium sulfate cut of 1E8 ascites was diluted to 10 ug/ml in PBS and 35 μl well were incubated for one hour at 37° C. in 96-well polyvinyl microtiter plate. Unoccupied binding sites were blocked with 1% nonfat dried milk. A neutrophil-acid extract, prepared without DFP as described above was diluted to 100 ug/ml and incubated with $^3$H DFP (3.3 nM at 3 uCi/uM, NEN) for thirty minutes at RT. The extract was then added (35 ul/well) to 1E8-precoated wells or wells precoated with an irrelevant mAb or with anti-MPO mAb as controls. After a four-hour incubation period at RT, wells were washed in PBS, dried, cut and immersed in betafluor and counted in a beta counter. The tritiated DFP bound only to the wells containing mAb 1E8.

Isoelectric focusing was performed in 0.75 mm thick gels using a vertical gel apparatus (Hoeffer Scientific) and a pH range 3.5-11. Gels were run at 2.5 mA constant current for 16 hours at 4° C., fixed, stained with Coomassie Blue R-250 and destained.

Indirect Solid Phase Immunoassay for Wegener's Granulomatosis

Microtiter TM wells are pre-coated with an ammonium sulfate cut of mAb 1E8, exposed to neutophil-acid extract (prepared as described above), and allowed to incubate for 4 hours. Wells are washed with PBS and exposed to test serum at 1:100 dilution in a total volume of 35 μl. After 60 minutes at RT the wells are washed with PBS and developed with $^{125}$I-labeled goat anti-human Ig antibody (preabsorbed to mouse IgG). Wells are cut, dried, and counted in a gamma counter. The $^{125}$I labeled goat-anti-human Ig antibody may be replaced with an anti-human Ig antibody conjugated to an enzyme or other radiometric or nonradiometric marker.

The assay may be provided in a convenient kit containing mAb 1E8 bound to microtiter wells (or a similar substrate) and other reagents needed to perform the assay.

Direct Solid Phase Immunoassay for Wegener's Granulomatosis p29 is affinity purified from neutrophil-acid extracts as described above. Purified p29 is coated onto microtiter TM wells. Serum (35 μl of a 1:100dilution) from a patient is added to the microtiter TM well and allowed to incubate for 60 minutes. The microtiter TM wells are washed with PBS and developed with a radiolabeled, enzyme conjugated, or otherwise labeled anti-Ig antibody.

The assay may be provided in a convenient kit containing p29 bound to microtiter TM wells (or other suitable substrates) and other reagents needed to perform the assay.

Production of Additional Monoclonal Antibodies Against p29 Protein

Our discovery that the circulating autoantibodies in the serum of patients with Wegener's granulomatosis are directed against the protein we have identified, p29, makes possible the routine production of monoclonal antibodies which are specific for p29. Such antibodies can be generate according to the procedure described above, or by an even simpler procedure, as follows.

Serum derived from any patient with Wegener's granulomatosis is contacted with lysed neutrophils, and the resulting immunorecipitate isolated; this precipitate will contain the p29 protein complexed with antibody. This immunoprecipitate is used to immunize animals, e.g., mice, many of which then produce antibodies to the p29 protein. The culture supernatants from hybridomas made based on such immunizations are then screened for those containing monoclonal antibodies which bind to lysate from normal neutrophils. Recognition of the p29 protein is comfirmed by Western blotting, as described above.

Cloning of the Gene for p29

The p29 N-terminal amino acid sequence information recited above will render cloning of the gene encoding that protein routine, particularly in view of the small size of the protein. The N-terminal sequence information will be used to make synthetic oligonucleotides, which will be used to obtain cDNA encoding the p29 protein, according to standard techniques, i.e., screening of cDNA library from neutrophils.

Other embodiments are within the following claims.

What is claimed is:

1. A substantially pure protein having the following characteristics:
   (a) it is found in neutrophils;
   (b) it has a mass of approximately 29 kD as determined by SDS-PAGE;
   (c) it is capable of binding diisopropylfluorophosphate;
   (d) it has a pI of approximately 9.2-9.4;

(e) it is capable of binding to autoantibodies present in the sera of individuals afflicted with Wegener's granulomatosis; and (f) it has the N terminal sequence Ile Val-Gly-Gly-His-Glu-Ala-Gln-Pro-His-Ser-X-Pro-Tyr-Met-Ala-Ser-Leu-Gln-Met, where X is unknown.

2. A monoclonal antibody having binding specificity for the protein of claim 1.

3. A method of detecting autoantibodies in a biological fluid, said autoantibodies being diagnostic of the presence of Wegener's granulomatosis, comprising:

(a) contacting said biological fluid with the protein of claim 1; and (b) detecting immune complexes formed as a measure of the presence of said autoantibodies.

4. A method of detecting autoantibodies in a biological fluid, said autoantibodies being diagnostic of the presence of Wegener's granulomatosis, comprising:

(a) contacting the monoclonal antibody of claim 2 with its antigen;

(b) contacting any immune complexes formed in step (a) with said biological fluid; and (c) detecting the binding of said autoantibodies to said immune complexes formed in (a) as a measure of the presence of said autoantibodies in said biological fluid.

* * * * *